(12) United States Patent
Miyata et al.

(10) Patent No.: US 11,974,040 B2
(45) Date of Patent: Apr. 30, 2024

(54) ENDOSCOPE PROCESSOR, STORAGE MEDIUM, AND CONTROL METHOD OF FOCUSING LENS

(71) Applicant: OLYMPUS MEDICAL SYSTEMS CORP., Tokyo (JP)

(72) Inventors: Akihiro Miyata, Hachioji (JP); Toshiaki Mikami, Akishima (JP); Koichiro Yoshino, Mitaka (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 120 days.

(21) Appl. No.: 17/945,170

(22) Filed: Sep. 15, 2022

(65) Prior Publication Data

US 2023/0084274 A1 Mar. 16, 2023

(30) Foreign Application Priority Data

Sep. 16, 2021 (WO) .................. PCT/JP2021/034180

(51) Int. Cl.
*H04N 23/67* (2023.01)
*A61B 1/00* (2006.01)
(Continued)

(52) U.S. Cl.
CPC ....... *H04N 23/675* (2023.01); *A61B 1/00006* (2013.01); *H04N 23/56* (2023.01); *H04N 23/667* (2023.01); *H04N 23/672* (2023.01); *A61B 1/00009* (2013.01); *A61B 1/07* (2013.01); *H04N 23/555* (2023.01)

(58) Field of Classification Search
CPC .... H04N 23/675; H04N 23/56; H04N 23/667; H04N 23/672; H04N 23/555;
(Continued)

(56) References Cited

U.S. PATENT DOCUMENTS 10,517,467 B2 * 12/2019 Mikami ........... A61B 1/000095
2007/0055104 A1 * 3/2007 Kumei ............... A61B 1/00188
600/176

(Continued)

FOREIGN PATENT DOCUMENTS

EP 3514595 A1 7/2019
JP 3980284 B2 9/2007
(Continued)

OTHER PUBLICATIONS

English Abstract of US 2022159193 A1, dated May 19, 2022 issued to Mizuochi.

*Primary Examiner* — Jared Walker
(74) *Attorney, Agent, or Firm* — Scully, Scott, Murphy & Presser, P.C.

(57) ABSTRACT

An endoscope processor includes a processor that can be connected to an endoscope including a moving mechanism of a focusing lens included in an objective optical system and an image pickup apparatus. The processor is configured to determine whether or not a transition has been made from a screening state to a proximity state based on positional information of the focusing lens and an image in a proximity determination mode when a variation in an image height in an effective image range with control of the moving mechanism is 1% or less, and when it is determined that a transition has been made to the proximity state, the processor is configured to end the proximity determination mode and control the moving mechanism in an autofocus mode.

12 Claims, 9 Drawing Sheets

(51) Int. Cl.
    *A61B 1/07*         (2006.01)
    *H04N 23/56*        (2023.01)
    *H04N 23/667*       (2023.01)
    *H04N 23/50*        (2023.01)

(58) Field of Classification Search
    CPC ............... H04N 23/67; A61B 1/00006; A61B
                1/00009; A61B 1/07; A61B 1/00188;
                G02B 23/26; G02B 23/2423
    See application file for complete search history.

(56) References Cited

U.S. PATENT DOCUMENTS

2014/0300716 A1* 10/2014 Tsuruoka ............... G03B 13/36
                                                    348/65
2014/0300799 A1* 10/2014 Yoshino ................ H04N 23/69
                                                    348/347
2017/0230567 A1*  8/2017 Takao ................... H04N 25/445
2018/0316871 A1* 11/2018 Yoshino ........... A61B 1/000095
2019/0167080 A1*  6/2019 Murase ................. A61B 1/0655
2019/0216301 A1*  7/2019 Okazaki .................. G02B 7/28
2019/0281227 A1   9/2019 Hirano et al.

FOREIGN PATENT DOCUMENTS

| JP | 5882745 B2    | 3/2016  |
|----|---------------|---------|
| JP | 2016195772 A  | 11/2016 |
| JP | 6177387 B2    | 8/2017  |
| JP | 2019102986 A  | 6/2019  |
| JP | 2020116147 A  | 8/2020  |
| JP | 2022078513 A  | 5/2022  |
| WO | 2018100885 A1 | 6/2018  |
| WO | 2020095366 A1 | 5/2020  |

\* cited by examiner

ENDOSCOPE PROCESSOR, STORAGE MEDIUM, AND CONTROL METHOD OF FOCUSING LENS

CROSS REFERENCE TO RELATED APPLICATION

This application claims benefit of International Application No. PCT/JP2021/034180 filed on Sep. 16, 2021, the entire contents of which are incorporated herein by this reference.

BACKGROUND OF THE INVENTION

1. Field of the Invention

The present invention relates to an endoscope processor that moves a focusing lens of an endoscope with a moving mechanism to acquire an image, a storage medium that stores a program for controlling the endoscope, and a control method of the focusing lens.

2. Description of the Related Art

As a size of a single pixel decreases due to advances in high-pixelation of an image pickup device, a depth of field becomes shallower. Advances in high-pixelation of an image pickup device have also been made in endoscopes, and a position of a subject may be moved outside of the depth of field during image pickup. Endoscopes equipped with an autofocus function are proposed in order to accommodate such cases.

Observation of a subject by an endoscope is broadly classified into two observation scenes.

One observation scene is an observation scene of a screening state for observing a subject in a wide distance range from a distant view to a close view and discovering a lesion. In the screening state, a position of a focusing lens is preferably fixed to a far point end so that a distance range as wide as possible from a distant view to a close view comes into focus.

Another observation scene is an observation scene of a proximity state in which, in order to diagnose the lesion discovered in the screening state in greater detail, a distal end portion of an insertion portion of the endoscope is brought close to the lesion. In the proximity state, autofocus is preferably run so that the lesion is continuously kept in focus.

When autofocus runs in the screening state, since a distance range to a subject portion that is in focus changes, it may become difficult to find a lesion and a user may experience stress. Therefore, a technique of preventing unnecessary autofocus is conventionally proposed.

For example, Japanese Patent No. 6177387 discloses a technique of determining whether an observation state is a screening observation state or a proximity magnified observation state based on a variation amount of a contrast value with respect to time, automatically switching to autofocus control when the observation state is determined to be the proximity magnified observation state, and starting autofocus control.

SUMMARY OF THE INVENTION

An endoscope processor according to an aspect of the present invention can be connected to an endoscope including: an objective optical system including a focusing lens and configured to form an optical image of a subject; a moving mechanism configured to move the focusing lens; and an image pickup apparatus configured to acquire an image by picking up the optical image, the endoscope processor including a processor, wherein the processor is configured to: control the moving mechanism in any one of an autofocus mode for automatically bringing the subject into focus and a proximity determination mode for determining whether or not a transition has been made from a screening state to a proximity state; execute the proximity determination mode when the autofocus mode is turned off; during the proximity determination mode, when a variation in an image height in an effective image range with control of the moving mechanism is 1% or less, determine whether or not a transition has been made from the screening state to the proximity state based on positional information of the focusing lens and a change in the image; and when it is determined that a transition has been made to the proximity state, end the proximity determination mode and control the moving mechanism in the autofocus mode.

A storage medium according to an aspect of the present invention is a non-transitory storage medium that is readable by a computer storing a program, the program causing a computer controlling an endoscope to: control a moving mechanism configured to move a focusing lens included in an objective optical system of the endoscope in any one of an autofocus mode for automatically bringing a subject into focus and a proximity determination mode for determining whether or not a transition has been made from a screening state to a proximity state; execute the proximity determination mode when the autofocus mode is turned off; during the proximity determination mode, when a variation in an image height in an effective image range is 1% or less, determine whether or not a transition has been made from the screening state to the proximity state based on positional information of the focusing lens and a change in an image acquired by an image pickup apparatus included in the endoscope; and when it is determined that a transition has been made to the proximity state, end the proximity determination mode and control the moving mechanism in the autofocus mode.

A control method of a focusing lens according to an aspect of the present invention includes: acquiring an image from an endoscope; acquiring positional information of a focusing lens of the endoscope; when a variation in an image height in an effective image range is 1% or less during control of a moving mechanism of the focusing lens of the endoscope in a proximity determination mode, determining whether or not a transition has been made from a screening state to a proximity state based on positional information of the focusing lens and a change in the image; and when it is determined that a transition has been made to the proximity state, ending the proximity determination mode and controlling the moving mechanism in an autofocus mode.

DETAILED DESCRIPTION OF THE PREFERRED EMBODIMENTS

Hereinafter, embodiments of the present invention will be described with reference to the drawings. However, it is to be understood that the present invention is not limited to the embodiments described below.

First Embodiment

Figure 1:
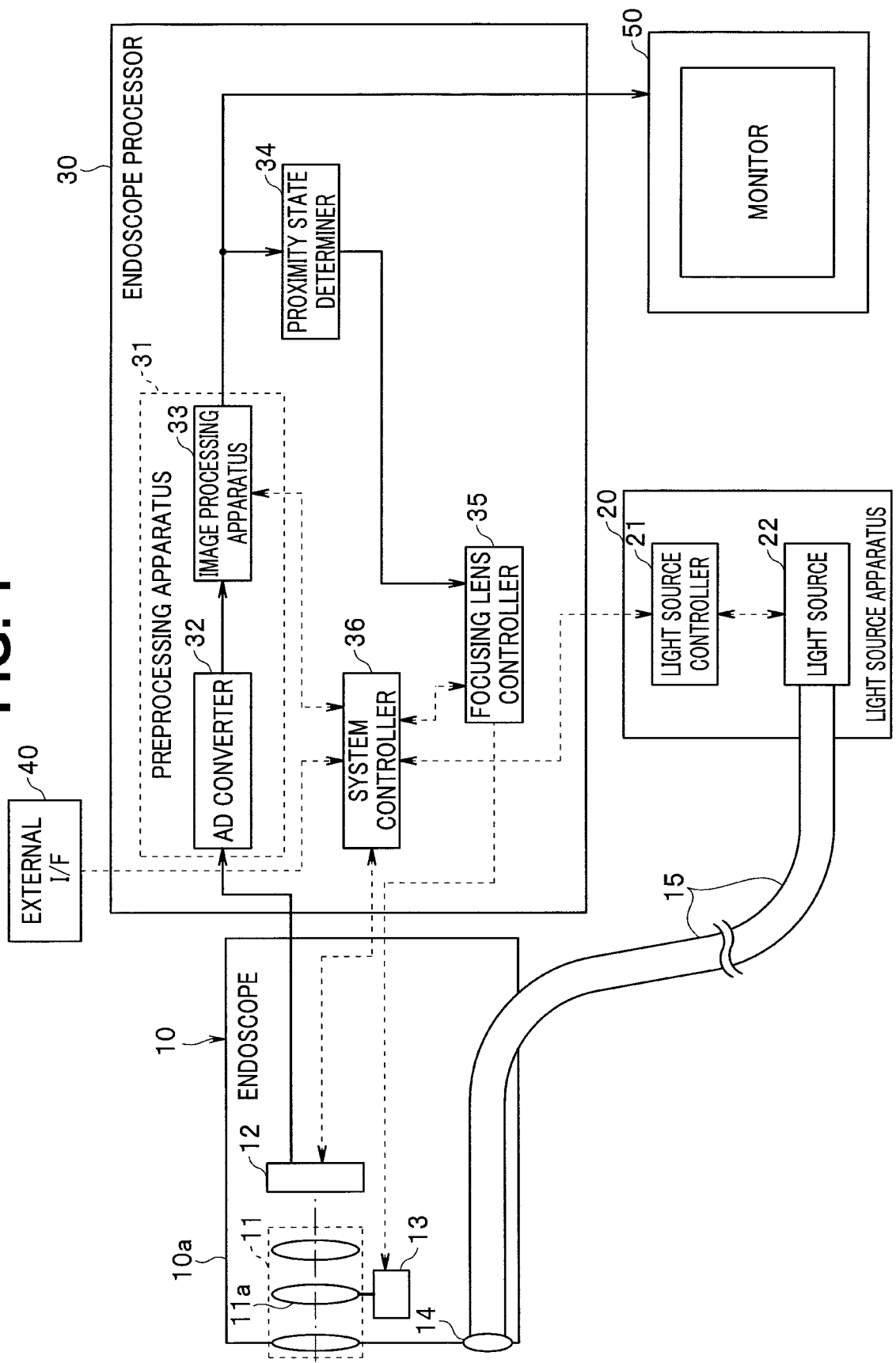
FIG. 1 is a block diagram showing structural and functional components of an endoscope system according to a first embodiment of the present invention.

FIGS. 1 to 6 represent a first embodiment of the present invention, in which FIG. 1 is a block diagram showing structural and functional components of an endoscope system according to the first embodiment. In FIG. 1 (and FIGS. 8 and 11 to be described later to which a similar description also applies), a solid arrow mainly indicates a flow of an image signal and a dotted arrow mainly indicates a flow of a control signal.

The endoscope system includes an endoscope 10, a light source apparatus 20, an endoscope processor 30, an external interface (external I/F) 40, and a monitor 50.

The endoscope 10 includes an insertion portion 10a that is inserted into an object. In this case, the object into which the insertion portion 10a is inserted may be a living object such as a person/human being or an animal or a non-living object such as a machine or a building.

The endoscope 10 is configured as an electronic endoscope and a distal end portion of the insertion portion 10a is provided with an objective optical system 11, an image pickup device 12, a moving mechanism 13, and an illumination lens 14.

The objective optical system 11 forms an optical image of a subject in the object on the image pickup device 12. The objective optical system 11 includes a focusing lens 11a and a position P of the focusing lens 11a is movable along an optical axis of the objective optical system 11. When the position P of the focusing lens 11a is moved, an in-focus portion of the subject (a subject portion that is in focus) in the optical image formed on the image pickup device 12 changes.

The subject according to the present invention refers to a portion which a user wishes to observe. For example, in a screening mode, an entire organ becomes the subject. In a proximity observation mode, a portion suspected to have a lesion such as a polyp, an inflammation, a tumor, angiogenesis, a portion with mucosal deformation, or a partially discolored portion becomes the subject.

The image pickup device 12 constitutes an image pickup apparatus and has pixels being arranged in a two-dimensional shape that convert incident light into an electrical signal. The image pickup device 12 picks up an optical image formed by the focusing lens 11a and acquires an image, and outputs the image as, for example, an analog image pickup signal. For example, the image pickup device 12 performs image pickup in frame units and sequentially outputs image pickup signals related to images of a plurality of frames in a time series.

While examples of the image pickup device 12 include solid-state image pickup devices such as a CMOS (complementary metal-oxide semiconductor) image sensor and a CCD (charge coupled device) image sensor, the image pickup device 12 is not limited to a specific configuration. In addition, the image pickup device 12 may be any of a color image pickup device and a monochrome image pickup device. When the image pickup device 12 is a color image pickup device, the image pickup device 12 may include any of a primary color filter and a complementary color filter and a filter arrangement may be a Bayer arrangement or another filter arrangement. Furthermore, the image pickup device 12 may be an image pickup device adopting an image plane phase-difference detection AF system including a phase difference pixel that applies pupil division to light from the objective optical system 11 and receives the light. An example of the image pickup device 12 being an image pickup device adopting an image plane phase-difference detection AF system will be described later.

The moving mechanism 13 is a mechanism that moves the focusing lens 11a along the optical axis of the objective optical system 11. The moving mechanism 13 includes, for example, an actuator as a drive source.

The illumination lens 14 irradiates the subject with illuminating light transmitted via a light guide 15 to be described later.

The light guide 15 is disposed inside the endoscope 10 including the insertion portion 10a. An exit end of the light guide 15 opposes the illumination lens 14 and an incident end of the light guide 15 is connected to the light source apparatus 20.

The light source apparatus 20 includes a light source controller 21 and a light source 22.

The light source controller 21 controls a light amount of the light source 22 in accordance with control by a system controller 36 to be described later in the endoscope processor 30. As the control of the light amount of the light source 22 by the light source controller 21, for example, a control method such as control of emission luminance or control of a duty ratio in PWM (pulse width modulation) may be used as appropriate.

The light source 22 emits illuminating light from a light-emitting device. For example, the light source 22 may include a combination of one or more kinds of light-emitting devices such as an LED (light emitting diode) light source, a laser light source, and a xenon light source. However, light-emitting devices are not limited to the examples listed here and known techniques can be used as appropriate.

Illuminating light emitted from the light source 22 is incident to the incident end of the light guide 15. The light guide 15 transmits the illuminating light incident from the incident end to the exit end. The transmitted illuminating light is emitted from the exit end of the light guide 15 and applied to the subject from the illumination lens 14.

The endoscope processor 30 performs image processing on an image pickup signal acquired by the image pickup device 12 of the endoscope 10. In addition, the endoscope processor 30 may control not only the endoscope but also the entire endoscope system including a monitor or the like.

As hardware, the endoscope processor 30 includes a preprocessing apparatus 31 including an AD (analog/digital) converter 32 and an image processing apparatus 33, a proximity state determiner 34, a focusing lens controller 35, and the system controller 36.

Figure 2:
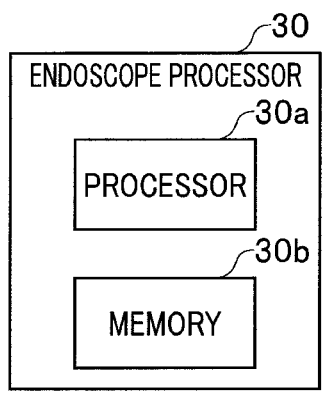
FIG. 2 is a block diagram showing an example of hardware components of an endoscope processor according to the first embodiment of the present invention.

While each functional component of hardware of the endoscope processor 30 is shown in the block diagram in FIG. 1, FIG. 2 is a block diagram showing an example of components of the endoscope processor 30 according to the first embodiment as a structural unit.

As shown in FIG. 2, the endoscope processor 30 includes a processor 30a and a memory 30b. For example, the processor 30a includes an ASIC (application specific integrated circuit) including a CPU (central processing unit) or the like, an FPGA (field programmable gate array), and the like.

For example, the memory 30b includes a volatile storage medium such as a RAM (random access memory) and a non-volatile storage medium such as a ROM (read only memory) (or an EEPROM (electrically erasable programmable read-only memory)). The RAM temporarily stores various types (kinds) of information such as an image being a processing object, a processing parameter during execution, and a user set value inputted from the external OF 40. The ROM stores, in a non-volatile manner, various types (kinds) of information such as a processing program (a computer program), a specified value of a processing parameter, and a user set value that should be stored even when power of the endoscope system is turned off.

As the processor 30a shown in FIG. 2 reads and executes the processing program stored in the memory 30b, various functions of the endoscope processor 30 as shown in FIG. 1 are fulfilled. However, all of or a part of the various functions of the endoscope processor 30 may be configured to be fulfilled by a dedicated electronic circuit.

In addition, while an example where the processing program is stored in the memory 30b has been described here, the processing program (or at least a part of the processing program) may be stored in a portable storage medium such as a flexible disk or a CD (compact disc)-ROM, a storage medium such as a hard disk or an SSD (solid state drive), a storage medium on a cloud, or the like. In this case, the processing program may be read from an external storage medium via the external OF 40 and stored in the memory 30b and the processor 30a may execute the processing program.

The AD converter 32 converts an analog image pickup signal outputted from the image pickup device 12 into a digital image and outputs the digital image to the image processing apparatus 33. When the image pickup device 12 is a digital image pickup device that outputs a digital image pickup signal, the AD converter 32 may be omitted.

The image processing apparatus 33 performs various kinds of image processing such as white balance processing, demosaicing (synchronization) processing, noise reduction processing, color conversion processing, gradation conversion processing, and contour enhancement processing with respect to images sequentially outputted in frame units from the AD converter 32. An image subjected to image processing by the image processing apparatus 33 is outputted to the proximity state determiner 34 and the monitor 50. For example, the image is also outputted to the focusing lens controller 35 via the proximity state determiner 34 (however, the focusing lens controller 35 may directly acquire the image from the preprocessing apparatus 31).

While an example where the image processing apparatus 33 outputs an image subjected to a series of image processing to the proximity state determiner 34 has been described here, the example is not limiting. In other words, since the proximity state determiner 34 performs a determination related to autofocus (AF) control, a real-time property is required. Therefore, the image outputted from the image processing apparatus 33 to the proximity state determiner 34 may be any of an image only subjected to AD conversion (RAW image), an image only subjected to AD conversion and demosaicing processing, and an image on which a few kinds of processing among a plurality of kinds of image processing have been omitted.

In addition, the image outputted from the image processing apparatus 33 to the proximity state determiner 34 and the focusing lens controller 35 need not be an entire image. For example, the system controller 36 being a control apparatus functions as a region setting unit and sets an AF region (which doubles as a region for determination to be used by the proximity state determiner 34 to determine whether or not a transition has been made to the proximity state) in at least a part of the image acquired by the image pickup device 12.

The system controller 36 may set the AF region in a central part of an image or a peripheral part of the image or may set a plurality of AF regions. In addition, the system controller 36 may arbitrarily set the AF region in accordance with, for example, an input from the external OF 40 in accordance with a user operation.

Alternatively, the system controller 36 may detect a specific subject or a portion (for example, a lesion) of the subject in the image and move the AF region so as to follow a movement of the specific subject or the portion of the subject. In addition, the system controller 36 may detect a region (for example, a properly-exposed region) in the image which a user is likely to focus on and set the detected region as the AF region.

Based on information on the position P of the focusing lens 11a and the image outputted from the image processing apparatus 33, the proximity state determiner 34 determines whether or not a transition has been made from a state (a screening state) where a distal end portion of the insertion portion 10a of the endoscope 10 is not in proximity to the subject to a state (a proximity state) where the distal end portion is in proximity to the subject. The distal end portion as used here refers to a predetermined region including the objective optical system 11. When the proximity state determiner 34 determines that a transition has been made to the proximity state, the proximity state determiner 34 outputs an AF start signal to the focusing lens controller 35.

The focusing lens controller 35 transmits a control instruction to the moving mechanism 13 and causes the moving mechanism 13 to move the focusing lens 11*a*. The focusing lens controller 35 causes the moving mechanism 13 to move the focusing lens 11*a* by controlling the moving mechanism 13 in any of an AF (autofocus) mode (AF control mode) for automatically bringing the subject into focus and a proximity determination mode (a control mode for proximity state determination) for determining whether or not a transition has been made to the proximity state.

Observation of a subject by an endoscope is broadly classified into two observation scenes.

One observation scene is an observation scene of a screening state. An observation scene of a screening state is a scene for observing a subject in a wide distance range from a distant view to a close view and discovering a lesion. Fixing the position P of the focusing lens 11*a* to a far point end Pf (refer to FIG. 3 and FIG. 5) or a vicinity of the far point end is preferable as a screening state because a wide distance range from a distant view to a close view comes into focus (in other words, a depth of field becomes as deep as possible). The depth of field becomes deepest when the position P of the focusing lens 11*a* is fixed to the far point end Pf.

When autofocus runs in the screening state, since a distance range to a subject portion that is in focus changes, a portion may be created where it is difficult to find a lesion. In addition, a change in a subject portion that is in focus may give a user stress. Therefore, in the screening state, the focusing lens controller 35 basically performs control in the proximity determination mode so as to prevent autofocus from running.

Another observation scene is an observation scene of a proximity state. When a lesion is discovered in the screening state, the distal end portion of the insertion portion 10*a* is brought close to the lesion in order to diagnose the discovered lesion in greater detail. In the proximity state, the distal end portion of the insertion portion 10*a* is more proximal to the subject than in the screening state. When the distal end portion of the insertion portion 10*a* is brought close to the lesion while keeping the position P of the focusing lens 11*a* fixed to the far point end Pf in the screening state, the lesion to be observed ends up falling outside of a depth of field range. Therefore, in the proximity state, the focusing lens controller 35 performs control in the AF mode so that autofocus runs and the lesion is continuously kept in focus.

The AF mode (AF control mode) is a mode of performing AF control and automatically moving the focusing lens 11*a* so that a subject is continuously kept in focus even if a distance from the distal end portion of the insertion portion 10*a* to the subject changes. AF control by the focusing lens controller 35 can be performed by any of contrast AF, phase-difference detection AF, or other AF control systems and is not limited to a specific system.

Contrast AF is performed by the focusing lens controller 35 by acquiring images of a plurality of frames while changing a position of the focusing lens 11*a* and, as well known, extracting contrast components from the images and moving the focusing lens 11*a* to a position where the contrast component is maximized.

In addition, when the image pickup device 12 is, for example, an image pickup device adopting an image plane phase-difference detection AF system, phase-difference detection AF is performed based on phase difference information acquired from a phase difference pixel included in the image pickup device 12. Using the image pickup device 12 adopting an image plane phase-difference detection AF system eliminates the need for a phase-difference detection AF sensor or the like that is separate from the image pickup device 12 and advantageously prevents a size of the endoscope 10 from increasing.

As described above, while autofocus is basically not run in the screening state, a determination must be made as to whether or not a transition of an observation scene has been performed from the screening state to the proximity state. Therefore, in the proximity determination mode (the control mode for proximity state determination), the focusing lens controller 35 is configured to perform control of slightly changing the position P of the focusing lens 11*a* to such a degree that observation by the user performing screening is not blocked (in other words, to such a degree that a distance range to a subject portion that is in focus does not substantially change) and to determine whether or not a transition has been made to the proximity state based on an image acquired by changing the position P. The processing in the proximity determination mode will be described in detail later.

When the focusing lens controller 35 receives an AF start signal from the proximity state determiner 34 during control in the proximity determination mode, the focusing lens controller 35 ends the proximity determination mode and performs control in the AF mode. When control in the AF mode is executed, AF control of the focusing lens 11*a* by the moving mechanism 13 is performed.

In addition, when the focusing lens controller 35 receives an AF end signal during control in the AF mode, the focusing lens controller 35 ends the AF mode and performs control in the proximity determination mode. In the present embodiment, it is assumed that the AF end signal is outputted when, for example, the proximity state determiner 34 determines that the proximity state has ended (a transition has been made to the screening state) (therefore, in the present embodiment, it can be said that the proximity state determiner 34 doubles as a screening state determiner 37 such as a screening state determiner 37 described later in a third embodiment). However, as will be described in the third embodiment, the screening state determiner 37 that outputs an AF end signal when determining that a transition has been made from the proximity state to the screening state may be provided separately from the proximity state determiner 34.

The system controller 36 is a control apparatus which receives an input signal from the external OF 40 and which controls the entire endoscope system including the image pickup device 12, the image processing apparatus 33, the focusing lens controller 35, and the light source controller 21. The system controller 36 outputs a control signal to the image pickup device 12 and causes the image pickup device 12 to acquire an image. The system controller 36 outputs a control signal based on various processing parameters necessary for image processing to the image processing apparatus 33 and causes the image processing apparatus 33 to perform processing of an image acquired from the image pickup device 12. The system controller 36 receives an image from the image processing apparatus 33 and transmits a control signal that gives the subject an appropriate brightness to the light source controller 21.

The external OF 40 is an interface to be operated by a user to perform input with respect to the endoscope system. The external OF 40 may include operation devices such as a keyboard, a mouse, and a trackball that are connected to the endoscope processor 30. In addition, the external OF 40 may include a connection interface or the like for connecting to an in-hospital system, a cloud, or the like.

For example, the external OF 40 includes a setup button for setting the AF mode/proximity determination mode and a setup button for setting a processing parameter to be used when image processing is performed by the image processing apparatus 33. At least a part of the setup buttons described above as being included in the external OF 40 may be provided on the endoscope processor 30 itself or provided in an operation portion consecutively provided on a side of a proximal end of the insertion portion 10a of the endoscope 10.

The monitor 50 displays images sequentially outputted from the endoscope processor 30. For example, by being displayed in a time series in frame units, the images are observed as a movie. An image outputted from the endoscope processor 30 may be an image created by superimposing, on an image subjected to image processing by the image processing apparatus 33, various types (kinds) of information such as text information and guide information for guiding operations of the endoscope 10.

The system controller 36 described above further transmits a control signal in accordance with the proximity determination mode or the AF mode to the focusing lens controller 35 and causes the focusing lens controller 35 to control the moving mechanism 13.

In the AF mode, the system controller 36 causes the focusing lens controller 35 to control the moving mechanism 13 so that a subject portion inside an AF region is continuously kept in focus.

In addition, in the proximity determination mode, the system controller 36 causes the focusing lens controller 35 to control the moving mechanism 13 so that, basically, the position P of the focusing lens 11a is at the far point end Pf.

However, as described above, in the proximity determination mode, the system controller 36 causes the focusing lens controller 35 to control the moving mechanism 13 so as to slightly change the position P of the focusing lens 11a from the far point end Pf in order to determine whether or not a transition has been made from the screening state to the proximity state.

Figure 3:
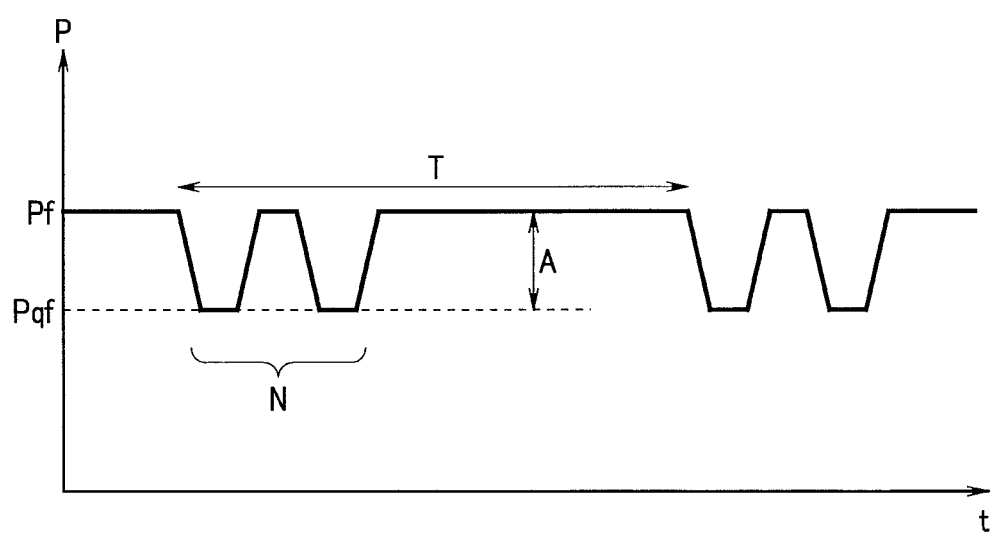
FIG. 3 is a timing chart showing an example of processing by which a focusing lens controller causes a moving mechanism to move a focusing lens based on control by a system controller according to the first embodiment of the present invention.

FIG. 3 is a timing chart showing an example of processing by which the focusing lens controller 35 causes the moving mechanism 13 to move the focusing lens 11a based on control by the system controller 36 according to the first embodiment.

As shown in FIG. 3, in the proximity determination mode executed in a screening state, the position P of the focusing lens 11a is basically fixed to the far point end Pf. However, in the proximity determination mode, the focusing lens controller 35 periodically or aperiodically performs a reciprocating operation of moving the focusing lens 11a from the far point end Pf toward a near point side by a slight amplitude A and once again returning the focusing lens 11a to the far point end Pf. Hereinafter, the position P (that differs from the far point end) to which the focusing lens 11a moves by the amplitude A from the far point end Pf toward the near point side will be referred to as a quasi-far point end Pqf.

In this case, as described above, the amplitude A is an amplitude that slightly changes the position P of the focusing lens 11a to such a degree that a distance range to a subject portion that is in focus does not substantially change. Since the subject portion that is in focus does not substantially change even when a reciprocating operation of the amplitude A is performed, observation by the user performing screening is not blocked.

When the focusing lens 11a moves to the quasi-far point end Pqf, the image pickup device 12 acquires an image of at least one frame. In order to shorten a time period in which the focusing lens 11a is at the quasi-far point end Pqf to further reduce an unnatural feeling that is experienced by the user, the image acquired by the image pickup device 12 at the quasi-far point end Pqf every time the reciprocating operation is performed once may be set to, for example, one frame.

FIG. 3 shows an example of performing the reciprocating operation of the amplitude A N-number of times (in the illustrated example, N=2) in each period T.

In the example shown in FIG. 3, at a start of the period T along a time t, the focusing lens 11a is moved to the quasi-far point end Pqf and an image of one frame is acquired. After image acquisition, the focusing lens 11a is immediately returned to the far point end Pf to acquire an image of a next one frame. Next, the focusing lens 11a is moved to the quasi-far point end Pqf to acquire an image of one frame and the focusing lens 11a is immediately returned to the far point end Pf. Subsequently, a plurality of images are continuously acquired in frame units at the far point end Pf until, for example, the period T ends.

In the proximity determination mode, the focusing lens controller 35 moves the focusing lens 11a to such a degree that image observation is not obstructed or, preferably, to such a degree that the movement of the focusing lens 11a is imperceptible to the user. An amount of movement of the focusing lens 11a is preferably an amount of movement that makes a variation in an image height h (refer to a field A in FIG. 4) in an effective image range EIA equal to or lower than 1%, more preferably equal to or lower than 0.5%, and even more preferably equal to or lower than 0.1%. The effective image range EIA according to the present invention is a range of an image shown on the monitor 50.

Figure 4:
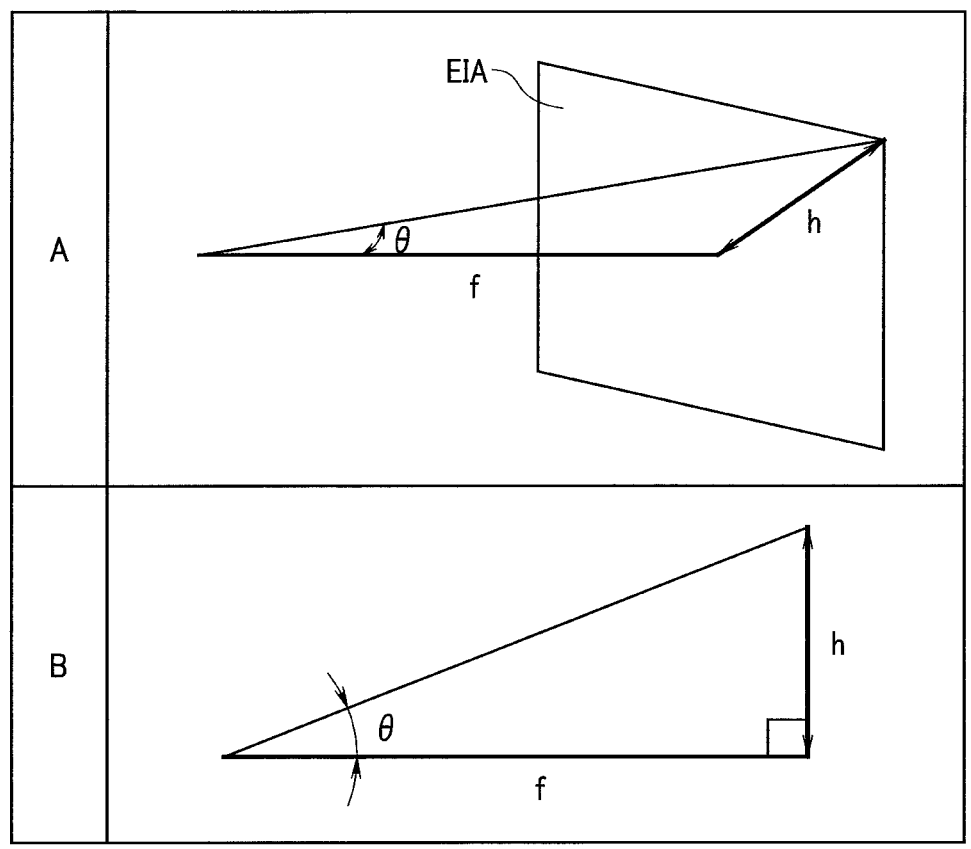
FIG. 4 is a diagram describing an image height in an effective image range according to the first embodiment of the present invention.

FIG. 4 is a diagram describing the image height h in the effective image range EIA according to the first embodiment. In FIG. 4, the field A shows a perspective view and a field B shows a plane which includes the image height h and which is perpendicular to the effective image range EIA. As shown in FIG. 4, the image height h can be obtained by Equation 1 from a half-angle of view θ and a focal length f.

$$h = f \times \tan\theta \qquad \text{[Equation 1]}$$

A direction in which the focusing lens 11a is moved is at least one direction, and the focusing lens 11a is preferably moved in a proximal direction, more preferably moved toward a far point after being moved in the proximal direction, and even more preferably reciprocated. For example, a periodic reciprocating operation of the focusing lens 11a as shown in FIG. 3 may be performed for each period T.

As described above, by setting the number of reciprocating operations such that N=2 and acquiring a plurality of images at the quasi-far point end Pqf, measurement error can be reduced as compared to a case where N=1 and an unnatural feeling that is experienced by the user can be reduced as compared to a case where N 3. However, the unnatural feeling experienced by the user can be further reduced by adopting N=1. In addition, a transition to the proximity state can be detected with higher accuracy by adopting N 3.

When periodically performing a reciprocating operation of the focusing lens 11a, the period T may be shortened to enable a transition to the proximity state to be detected at a time interval including as few frames as possible (in other words, in a state as close to real-time as possible). In addition, the amplitude A may be increased as much as possible within a range in which the user does not experience an unnatural feeling to enable a transition to the proximity state to be detected at higher accuracy.

On the other hand, when aperiodically performing a reciprocating operation of the focusing lens 11a, for example, the focusing lens 11a may be reciprocated at a random timing with a frame period as a unit.

In addition, an aperiodic reciprocating operation may be realized by performing a reciprocating operation of the focusing lens 11a when detecting that an acquired image is an image of a specific scene but not performing a reciprocating operation of the focusing lens 11a when not detecting that an acquired image is an image of the specific scene. In this case, the specific scene is a scene that is likely to be in the proximity state. Detection of the specific scene may be performed by, for example, an AI (artificial intelligence) having deep-learned an image of the proximity state. In addition, the detection of the specific scene may be performed based on a change in brightness of a plurality of images acquired in a time series and/or a motion vector detected from an image (refer to a description of the third embodiment to be provided later).

A start point when the focusing lens 11a is moved in the proximal direction or an end point when the focusing lens 11a is moved toward a far point is preferably within a predetermined range from the far point end and is more preferably the far point end.

Figure 5:
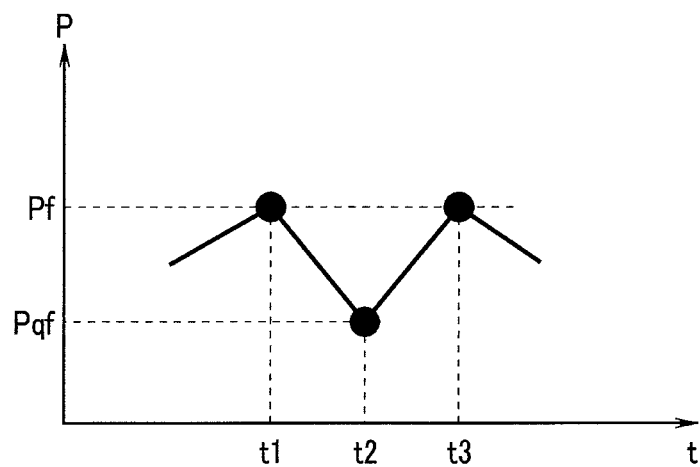
FIG. 5 is a timing chart showing an example of one reciprocating operation of the focusing lens from a far point end to a quasi-far point end according to the first embodiment of the present invention.
Figure 6:
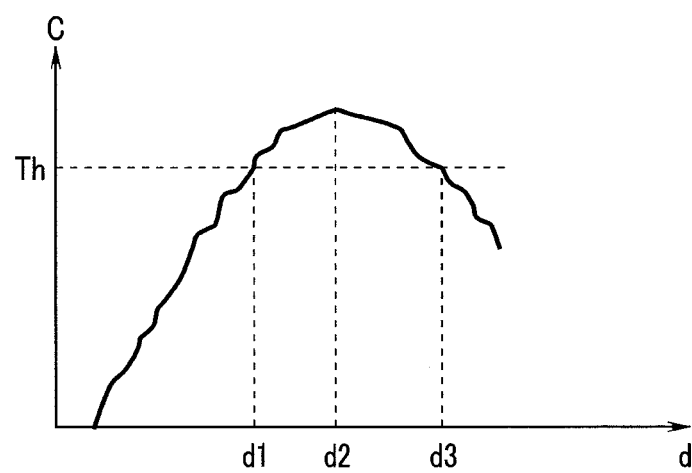
FIG. 6 is a graph showing an example of a contrast difference between a far point end image and a quasi-far point end image in accordance with a distance to a subject according to the first embodiment of the present invention.

Next, a method of determining whether or not a transition has been made from the screening state to the proximity state by performing a reciprocating operation of the focusing lens 11a will be described with reference to FIG. 5 and FIG. 6. FIG. 5 is a timing chart showing an example of one reciprocating operation of the focusing lens 11a from the far point end Pf to the quasi-far point end Pqf according to the first embodiment. FIG. 6 is a graph showing an example of a contrast difference C between a far point end image and a quasi-far point end image in accordance with a distance d to a subject according to the first embodiment.

In FIG. 5, it is assumed that a time point t1 and a time point t2 differ only by one frame period and that the time point t2 and a time point t3 also differ only by one frame period.

A far point end image (Pf: t1) is acquired at the time point t1 when the focusing lens 11a is at the far point end Pf, a quasi-far point end image (Pqf: t2) is acquired at the time point t2 when the focusing lens 11a is at the quasi-far point end Pqf, and a far point end image (Pf: t3) is acquired at the time point t3 when the focusing lens 11a is at the far point end Pf. In other words, the far point end image (Pf: t1), the quasi-far point end image (Pqf: t2), and the far point end image (Pf: t3) are a plurality of temporally-continuous images with different focus positions when performing a reciprocating operation of the focusing lens 11a.

The proximity state determiner 34 determines whether or not a transition has been made to the proximity state based on a change in an image when differentiating the focus position. More specifically, the proximity state determiner 34 calculates image information of a plurality of images with different focus positions. For example, as image information, the proximity state determiner 34 calculates a contrast of the far point end image (Pf: t1) and the quasi-far point end image (Pqf: t2). More specifically, the proximity state determiner 34 calculates a contrast value of each pixel inside an AF region that is a region in which image information is calculated and, further, calculates, for example, an average (or a sum or the like) of contrast values in the AF region as the contrast value of each image. The following description will be given on the assumption that the contrast value of an image refers to an average (or a sum) of contrast values in the AF region of the image.

Using an average or a sum has an advantage of reducing a calculation amount and suppressing an increase in cost due to an increase in buffer size. On the other hand, respectively comparing a contrast value of each pixel in the AF region among a plurality of temporally-continuous images with different focus positions has an advantage of enabling precise calculations and, in the present invention, the latter can also be adopted.

An image portion in a depth of field is in focus while an image portion outside of the depth of field is out of focus, and a contrast value of an image is high in an in-focus portion and low in an out-of-focus portion.

For example, an image portion in a central portion of the depth of field in the far point end image (Pf: t1) is also within the depth of field in the quasi-far point end image (Pqf: t2) for which the position P of the focusing lens 11a has been slightly changed and the image portion is in focus in both images. Therefore, there is hardly any difference in contrast values (simply referred to as a "contrast difference") between the far point end image (Pf: t1) and the quasi-far point end image (Pqf: t2).

In addition, an image portion that is significantly deviated from the depth of field in the far point end image (Pf: t1) is also significantly deviated from the depth of field in the quasi-far point end image (Pqf: t2) and the image portion is significantly out of focus in both images. Therefore, a contrast difference between the far point end image (Pf: t1) and the quasi-far point end image (Pqf: t2) is small.

On the other hand, a depth of field indicating a distance range to a subject portion that is in focus has a far point-side depth limit and a near point-side depth limit. For example, a vicinity of an outer side of the near point-side depth limit of the depth of field which is in an "out-of-focus state" in the far point end image (Pf: t1) changes to an "in-focus state" in the quasi-far point end image (Pqf: t2). In addition, a vicinity of an outer side of the far point-side depth limit of the depth of field which is in an "in-focus state" in the far point end image (Pf: t1) changes to an "out-of-focus state" in the quasi-far point end image (Pqf: t2). Therefore, the depth limit of the depth of field has a larger contrast difference between the far point end image (Pf: t1) and the quasi-far point end image (Pqf: t2) than the central portion of the depth of field and a portion significantly deviated from the depth of field.

FIG. 6 shows how the contrast difference C changes in accordance with the distance d to the subject.

For example, the contrast difference C is calculated as an absolute value of a value obtained by subtracting the contrast value of the far point end image (Pf: t1) from the contrast value of the quasi-far point end image (Pqf: t2).

A reason why an absolute value is calculated in this case is to avoid complications due to a change in a positive/negative of a sign in accordance with whether a depth limit is either a far point-side depth limit or a near point-side depth limit and which of the quasi-far point end image (Pqf: t2) and the far point end image (Pf: t1) is to be subtracted from the other of the quasi-far point end image (Pqf: t2) and the far point end image (Pf: t1). However, when performing case classification in accordance with signs, an absolute value need not be obtained. When performing case classification, for example, there may be cases where not only a local maximum value (refer to FIG. 6) to be described later but also a local minimum value must also be taken into consideration.

In the example shown in FIG. 6, the contrast difference C is equal to or larger than a threshold Th when the distance d to the subject ranges from d1 to d3, inclusive, and the contrast difference C takes a local maximum value when the distance d is d2 (d1<d2<d3).

For example, when the contrast difference C is equal to or larger than the threshold Th, a determination can be made that the AF region has changed from inside of the depth of field (a contrast of the AF region is relatively high) to outside of the depth of field (a contrast of the AF region is relatively low) (or from the outside of the depth of field to the inside of the depth of field) (in other words, a value of the threshold Th is set so as to enable the determination).

For example, when the contrast difference C is equal to or larger than the threshold Th, the proximity state determiner 34 determines that a transition is made from the screening state in which observation is performed to search for a lesion or the like while fixing the focusing lens 11a to the far point end Pf to the proximity state in which observation is performed in proximity to a specific lesion or the like.

While the contrast difference C is calculated by comparing the contrast value of the far point end image (Pf: t1) and the contrast value of the quasi-far point end image (Pqf: t2) with each other in the description given above, instead, the contrast difference C may be calculated by comparing the contrast value of the quasi-far point end image (Pqf: t2) and the contrast value of the far point end image (Pf: t3) with each other.

Alternatively, calculating the contrast difference C by comparing an average of the contrast value of the far point end image (Pf: t1) and the contrast value of the far point end image (Pf: t3) with the contrast value of the quasi-far point end image (Pqf: t2) further heightens a temporal correlation and increases accuracy of determination.

Furthermore, while a change in contrast values is obtained as a contrast difference in the description provided above, alternatively, a change in contrast values may be obtained as a ratio between contrast values (simply referred to as a "contrast ratio"). The contrast ratio may be any of a ratio between the contrast value of the far point end image (Pf: t1) and the contrast value of the quasi-far point end image (Pqf: t2), a ratio between the contrast value of the far point end image (Pf: t3) and the contrast value of the quasi-far point end image (Pqf: t2), and a ratio between an average of the contrast values of the far point end image (Pf: t1) and the far point end image (Pf: t3) and the contrast value of the quasi-far point end image (Pqf: t2).

In addition, while an example of fixing the position P of the focusing lens 11a to the far point end Pf in the screening state in order to attain a deepest depth of field has been described above as a preferable example, the position P of the focusing lens 11a is not limited to the far point end Pf. For example, in the screening state, on the basis of fixing the position P of the focusing lens 11a to a specific position (which may be a position other than the far point end Pf), the focusing lens controller 35 performs processing of slightly shifting the position P of the focusing lens 11a from the specific position. In addition, the proximity state determiner 34 may be configured to determine that a transition has been made from the screening state to the proximity state based on a plurality of images with different focus positions acquired at respective positions.

Note that phase difference information acquired from a phase difference pixel may be adopted instead of a contrast as image information used by the proximity state determiner 34 when making a determination.

Using phase difference information acquired from a phase difference pixel enables a distance to the subject to be acquired. A phase difference increases when the subject is not in focus, and a large phase difference results in improved ranging accuracy.

When acquiring images (for example, a far point end image and a quasi-far point end image) with different focus positions by causing the focusing lens 11a to perform a reciprocating operation, the far point-side depth limit of the depth of field more significantly moves out of focus in the quasi-far point end image and a phase difference increases, and ranging accuracy improves. Therefore, the proximity state determiner 34 may compare a distance calculated based on phase difference information acquired from a phase difference pixel of the quasi-far point end image with a threshold and determine that a transition has been made from the screening state to the proximity state when a state where the distance is longer than the threshold changes to a state where the distance is equal to or shorter than the threshold. As will be shown in a modification to be described later, whether or not a transition has been made to the proximity state may be determined by also taking into account a determination result by a reliability determiner 38 (refer to FIG. 7).

Accordingly, a determination that a transition is made from the screening state to the proximity state can be made and a transition from the proximity determination mode to the AF mode can be made at a stage slightly before an image portion at the far point-side depth limit in a far point end image deviates from the depth of field (in other words, a stage slightly before moving out of focus), as compared to the case where the focusing lens 11a is not caused to perform a reciprocating operation.

In addition, a difference or a ratio between phase differences of images (for example, a far point end image and a quasi-far point end image) before and after causing the focusing lens 11a to perform a reciprocating operation increases at a depth limit of the depth of field. Therefore, the proximity state determiner 34 may determine that a transition has been made from the screening state to the proximity state when, for example, the difference or the ratio between the phase difference of the far point end image and the phase difference of the quasi-far point end image changes from a state of being smaller than the threshold to a state of being equal to or larger than the threshold.

According to the first embodiment described above, the focusing lens 11a is caused to perform a slight reciprocating operation in an optical axis direction in the screening state, and a determination of whether or not a transition of a positional relationship between a subject and the endoscope is made from the screening state to the proximity state is performed based on a characteristic that a change in an image acquired at the depth limit of the depth of field is locally maximized. In addition, by turning off autofocus in the screening state where the subject is inside the depth of field and turning on autofocus when a transition is made from the screening state to the proximity state where the subject is in proximity, unnecessary autofocus can be prevented in the screening state.

Furthermore, since a determination is made based on a plurality of images acquired by causing the focusing lens 11a to perform a slight reciprocating operation in the optical axis direction, a dedicated subject distance detection apparatus or the like is no longer necessary and an increase in size of the endoscope can be prevented.

[Modification of First Embodiment]

In the first embodiment, whether or not a transition is made to the proximity state is determined based on a change in an image such as a contrast change. However, in addition to the technique according to the first embodiment, whether a change in an image when differentiating focus positions is a change resulting from a transition of the endoscope to the proximity state or a change based on another factor and the endoscope has not actually made a transition to the proximity state may be determined by also taking into account an image, a state of the endoscope, or a state of the subject.

Figure 7:
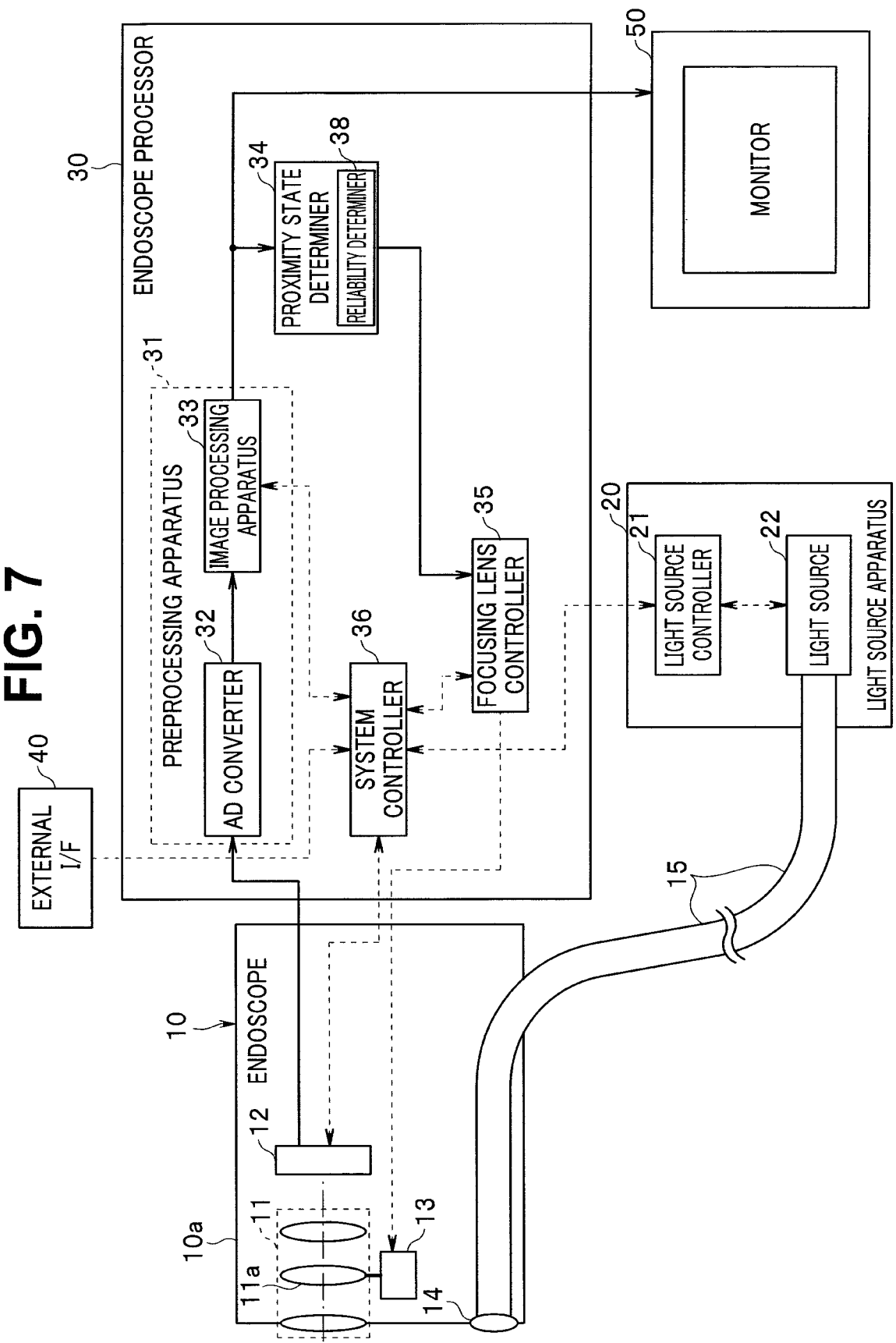
FIG. 7 is a block diagram showing structural and functional components of an endoscope system according to a modification of the first embodiment of the present invention.

Specifically, as shown in FIG. 7, the proximity state determiner 34 may include the reliability determiner 38. FIG. 7 is a block diagram showing structural and functional components of an endoscope system according to a modification of the first embodiment.

The reliability determiner 38 calculates reliability based on, for example, image information. Examples of image information include motion amount information, luminance information, contrast information, and color information.

By incorporating motion amount information into reliability determination, even though an image blur is created due to a motion of a distal end of the endoscope 10 and/or a subject being sudden, an erroneous determination that a transition has been performed from an image state to a proximity determination state can be prevented from being made. In this case, a transition to the autofocus mode is set not to be made when, for example, the motion amount is equal to or larger than a predetermined value. The motion amount is obtained by calculating a similarity between images of a previous frame and a present frame and calculating which image position in the present frame an image position in the previous frame has moved to.

By incorporating luminance information into reliability determination, an erroneous determination that a transition has been performed to a proximity determination state due to, for example, an increase in luminance caused by reflection from a bodily fluid or the like can be prevented from being made. In this case, a transition to the autofocus mode is set not to be made when, for example, the luminance is equal to or higher than a predetermined value.

By incorporating contrast information into reliability determination, an erroneous determination that a contrast value has changed and a transition has been performed to a proximity determination state as a result of, for example, the distal end of the endoscope 10 or a treatment instrument with a strong edge being reflected in an image can be prevented from being made. In this case, a transition to the autofocus mode is set not to be made when, for example, a contrast value at a position where the distal end of the endoscope 10 or the treatment instrument is reflected is equal to or higher than a predetermined value.

By incorporating color information into reliability determination, an erroneous determination that a contrast value has changed and a transition has been performed to a proximity determination state as a result of, for example, a treatment instrument, a mist, a bubble, or a liquid pool being reflected in an image or the distal end of the endoscope 10 being submerged in a liquid can be prevented from being made. In this case, a transition to the autofocus mode is set not to be made when, for example, a distance of a color of an image of the present frame with respect to a color distribution of each of the treatment instrument, the mist, the bubble, and the liquid pool in a color space is equal to or less than a predetermined value.

The reliability determiner 38 calculates reliability based on, for example, emission information. Examples of the emission information include a light amount, an emission period, and a wavelength of illuminating light. An example of the emission period is a charge readout period.

When proximity observation is performed, normally, a light amount of illuminating light applied to the subject decreases. Therefore, when the proximity state determiner 34 makes a determination of the proximity state despite the light amount being equal to or larger than a predetermined value, the determination may be assumed to be an erroneous determination and a transition to the autofocus state may not be made. The reliability determiner 38 acquires the light amount of the illuminating light emitted by the light source 22 from the light source controller 21 via, for example, the system controller 36.

When the endoscope system is designed to emit light during the charge readout period, there is a possibility that an image blur may occur and an erroneous determination that a transition is performed to the proximity determination state may be made. Therefore, when a determination of the proximity state is made from an image within a predetermined time period from a start of charge readout (during the charge readout period), the determination may be assumed to be an erroneous determination and a transition to the autofocus state may not be made.

Since the subject is often red, a contrast of an image obtained when a wavelength of illuminating light during frame-sequential emission is red tends to be low. Therefore, when a determination of the proximity state is made from an image of which a wavelength of illuminating light during frame-sequential emission is red, the determination may be assumed to be an erroneous determination and a transition to the autofocus state may not be made.

The reliability determiner 38 calculates reliability based on, for example, positional information of the focusing lens 11a. The positional information of the focusing lens 11a is a difference between a designated position of the focusing lens 11a transmitted by the proximity state determiner 34 or the focusing lens controller 35 to the moving mechanism 13 and an actual position. The actual position of the focusing lens 11a can be acquired from the moving mechanism 13 or the focusing lens controller 35.

The reliability determiner 38 may include an AI and may be configured to calculate reliability based on the image information described above by machine learning.

Second Embodiment

Figure 8:
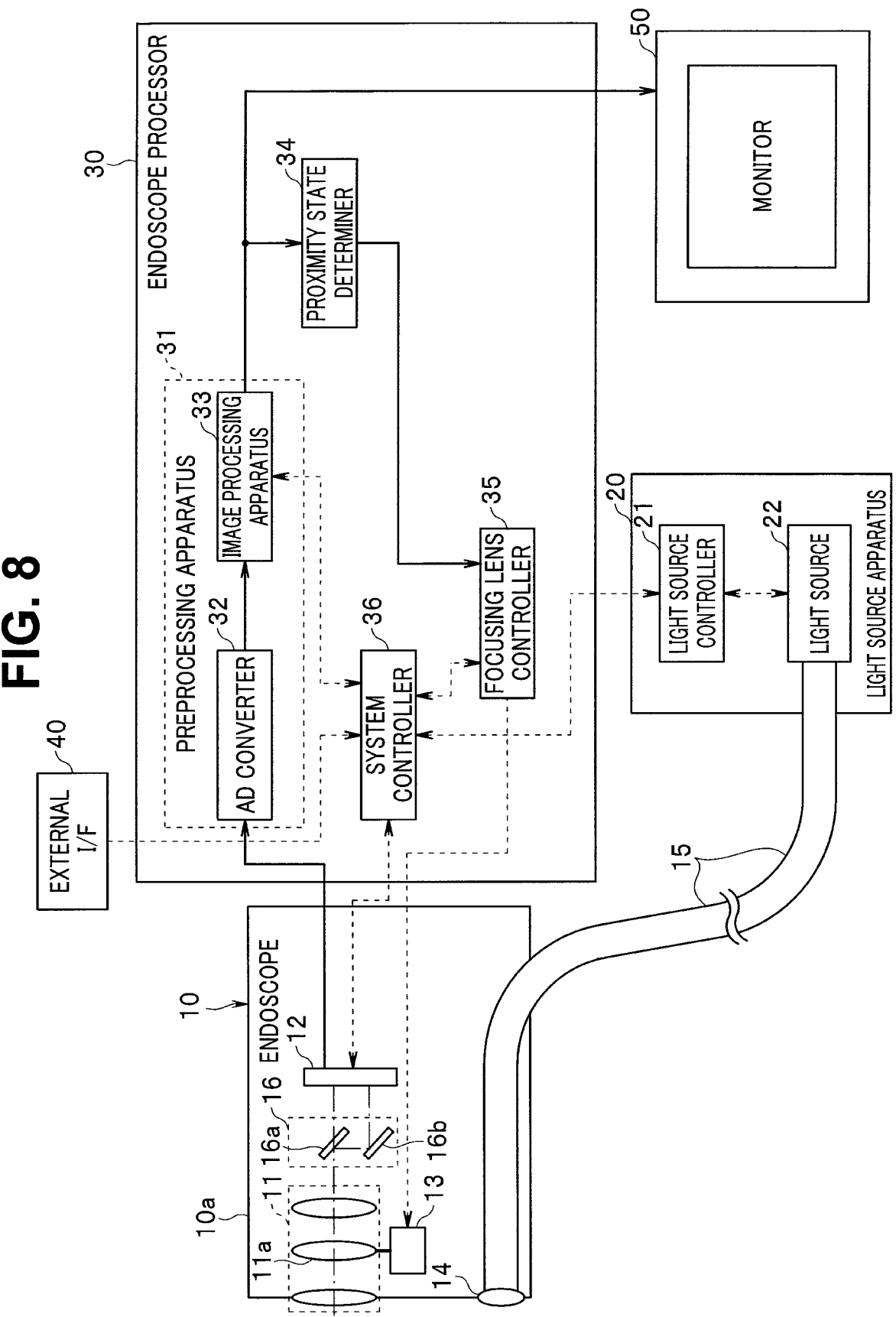
FIG. 8 is a block diagram showing structural and functional components of an endoscope system according to a second embodiment of the present invention.
Figure 9:
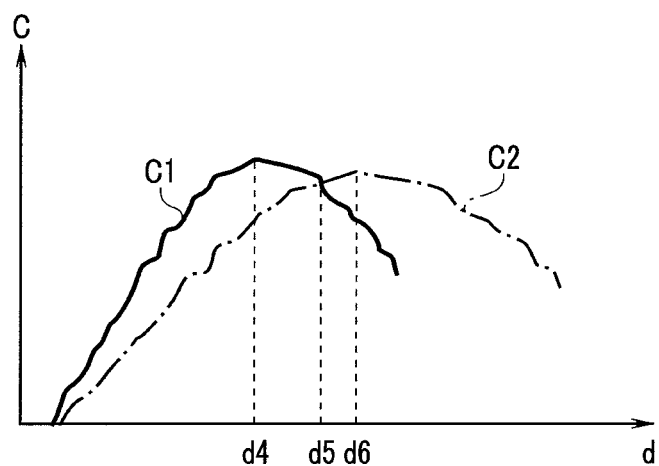
FIG. 9 is a graph showing an example where a magnitude relationship occurs between a contrast difference of a first image and a contrast difference of a second image due to a reciprocating operation of a focusing lens in the endoscope system according to the second embodiment of the present invention.
Figure 10:
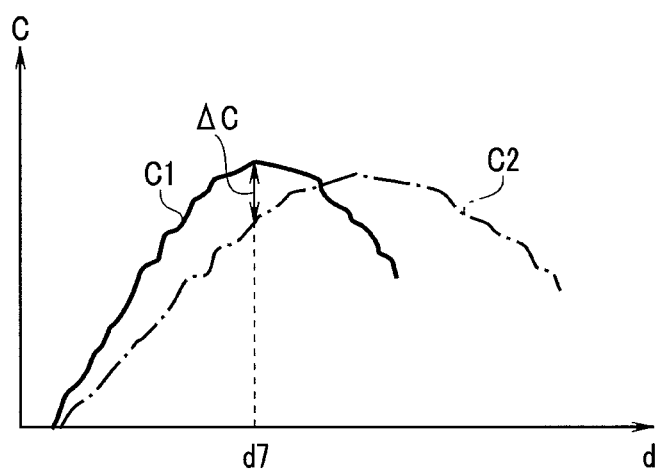
FIG. 10 is a graph showing an example where a difference between contrast differences is used for determination when a contrast difference of a first image and a contrast difference of a second image change due to a reciprocating operation of the focusing lens in the endoscope system according to the second embodiment of the present invention.

FIGS. 8 to 10 represent a second embodiment of the present invention, in which FIG. 8 is a block diagram showing structural and functional components of an endoscope system according to the second embodiment. In the second embodiment, portions similar to the first embodiment and the modification of the first embodiment described above will be denoted by same reference signs or the like and descriptions of such portions will be omitted as appropriate, and only differences will be mainly described.

An endoscope system according to the present embodiment adopts an EDOF (extended depth of field) technique. In an EDOF, a luminous flux from the objective optical system 11 is divided into a plurality of (for example, two) luminous fluxes by a dividing optical system 16, and optical path lengths of the plurality of luminous fluxes are differentiated to form a plurality of optical images. The plurality of formed optical images are simultaneously picked up by the image pickup device 12 to acquire a plurality of images with different focus positions, and by compositing portions in focus in the plurality of images, a composite image with an enlarged depth of field is generated.

Specifically, the endoscope 10 according to the present embodiment further includes the dividing optical system 16. For example, the dividing optical system 16 is arranged between the objective optical system 11 and the image pickup device 12.

As an example, the dividing optical system 16 includes a semi-transparent mirror 16a and a reflecting mirror 16b. A luminous flux emitted from the objective optical system 11 is partially transmitted and partially reflected by the semi-transparent mirror 16a. The luminous flux reflected by the semi-transparent mirror 16a is further reflected by the reflecting mirror 16b toward the image pickup device 12.

The luminous flux transmitted by the semi-transparent mirror 16a forms an image in a part of the image pickup device 12 and the luminous flux reflected by the reflecting mirror 16b forms an image in another part of the image pickup device 12. Due to the configuration described above, an optical image formed in a part of the image pickup device 12 and an optical image formed in another part of the image pickup device 12 have different optical path lengths.

The image pickup device 12 simultaneously picks up the optical image formed in a part and the optical image formed in another part to acquire a plurality of images. Each of the plurality of images acquired at this point has a different focus position.

Note that a configuration of the dividing optical system 16 shown in FIG. 8 is a simple model and an actual configuration of the dividing optical system 16 may differ from the configuration shown in FIG. 8. For example, the semi-transparent mirror 16a and the reflecting mirror 16b may be configured as mirror surfaces of a prism. In addition, the semi-transparent mirror 16a may be configured as a polarizing beam splitter surface and may further include a depolarizing plate for eliminating polarization in a direction of polarization and a wave plate that converts linearly polarized light into circularly polarized light and vice versa. Furthermore, a luminous flux is not limited to being divided into two and may be divided into three or more. Moreover, instead of forming images in different portions of the same image pickup device 12, the plurality of divided luminous fluxes may each form an image on each of a plurality of different image pickup devices.

In addition, the image processing apparatus 33 performs image composition processing of compositing portions that are in focus with respect to a plurality of images with different focus positions that are simultaneously acquired by the image pickup device 12 to generate a composite image with an enlarged depth of field.

Hereinafter, for the sake of brevity, a case where the number of images that are simultaneously acquired is two will be described.

The proximity state determiner 34 determines whether or not a transition has been made from the screening state to the proximity state using, for example, two simultaneously acquired images with different focus positions (for example, referred to as a first image and a second image). In this case, with the exception of two images being acquired simultaneously and the fact that a reciprocating operation of the focusing lens 11a is not required, whether or not a transition has been made from the screening state to the proximity state can be determined by performing the processing described above in the first embodiment based on the two images.

In addition, in a similar manner to the first embodiment described above, the proximity state determiner 34 may further acquire two images by causing the focusing lens 11a to perform a reciprocating operation and determine whether or not a transition has been made from the screening state to the proximity state based on a total of four images.

In this case, to make a determination, the proximity state determiner 34 uses a total of four images including two images (for example, referred to as a 1a-th image and a 2a-th image) acquired before shifting the focusing lens 11a (or when returned to an original position after being shifted) and two images (for example, referred to as a 1b-th image and a 2b-th image) acquired in a state where the focusing lens 11a has been shifted.

Among the two images simultaneously acquired by the image pickup device 12, "1" is attached to an image (a near point image) acquired from an optical image with a long optical path length from the objective optical system 11 to the image pickup device 12 and "2" is attached to an image (a far point image) acquired from an optical image with a short optical path length. In addition, "a" is attached to an image acquired at a focus position of the far point end Pf before shifting the focusing lens 11a and "b" is attached to an image acquired at a focus position of the quasi-far point end Pqf in a shifted state.

When the proximity state determiner 34 uses, for example, contrast information of a total of four images acquired two by two in a temporally-continuous manner to make a determination, a characteristic is used in that a distance at which the near point image and the far point image have an equal contrast difference between images acquired before shifting the focusing lens 11a and in a shifted state of the focusing lens 11a is near a depth limit of the depth of field and is a proximity state.

Let averages of contrast values in AF regions of the 1a-th, 1b-th, 2a-th, and 2b-th images be respectively represented by C1a, C1b, C2a, and C2b. In this case, for example, the proximity state determiner 34 calculates a contrast difference C1=(C1b−C1a) between the 1a-th image and the 1b-th image and a contrast difference C2=(C2b−C2a) between the 2a-th image and the 2b-th image. As already described in the first embodiment, an absolute value may be calculated when calculating the contrast differences C1 and C2.

FIG. 9 is a graph showing an example where a magnitude relationship occurs between the contrast difference C1 of the first image and the contrast difference C2 of the second image due to a reciprocating operation of the focusing lens 11a in the endoscope system according to the second embodiment.

In the example shown in FIG. 9, the contrast difference C1 has a local maximum value when the distance d to the subject is d4 while the contrast difference C2 has a local maximum value when the distance d to the subject is d6 (d4<d6), and a magnitude relationship between the contrast difference C1 and the contrast difference C2 is reversed when the distance d to the subject is d5 (d4<d5<d6).

The proximity state determiner 34 determines that when the distance d to the subject is d5, the distance d is near the depth limit of the depth of field and a transition has been made from the screening state to the proximity state.

In the determination method described in the first embodiment, a threshold must be set with respect to a contrast difference and a magnitude relationship between the contrast difference and the threshold must be determined. By comparison, in the case of the determination method based on a magnitude relationship between contrast differences described above, since a determination result is not dependent on a magnitude of a contrast in a texture of a subject or the like, determination accuracy can be enhanced.

In addition, according to the determination method, since a transition made to the proximity state can be determined before deviating from the depth limit of the depth of field as shown in FIG. 9, a transition can be made from the proximity determination mode to the AF mode slightly before a subject being observed moves out of focus.

FIG. 10 is a graph showing an example where a difference between contrast differences is used for determination when the contrast difference C1 of the first image and the contrast difference C2 of the second image change due to a reciprocating operation of the focusing lens 11a in the endoscope system according to the second embodiment.

In this case, after calculating the contrast difference C1=(C1b−C1a) and the contrast difference C2=(C2b−C2a), the proximity state determiner 34 further calculates a difference ΔC=C1−C2 between the contrast differences (the example shown in FIG. 10 represents the ΔC when distance d=d7). The proximity state determiner 34 sets a threshold with respect to ΔC and determines that a transition has been made to the proximity state when ΔC is equal to or more than the threshold.

While the difference ΔC=C1−C2 between contrast differences is calculated in this case, for example, a ratio C1/C2 between the contrast differences may be calculated instead and the ratio C1/C2 may be compared with an appropriate threshold.

Note that, even in the present embodiment, phase difference information acquired from a phase difference pixel may be adopted instead of a contrast as image information used by the proximity state determiner 34 when making a determination.

When, for example, four images are acquired as described above by performing simultaneous acquisition of a plurality of images with different focus positions while shifting a position of the focusing lens 11a, a reliability of a calculation result of a phase difference may be calculated based on the position of the focusing lens 11a, a result of a comparison between phase differences of two images acquired by moving the focusing lens 11a, and the like, and the proximity state determiner 34 may determine that a transition has been made to the proximity state using only a phase difference with high reliability.

In addition, the proximity state determiner 34 may be configured to determine that a transition has been made to the proximity state based on a composite image of an enlarged depth of field that is outputted from the image processing apparatus 33. In this case, the proximity state determiner 34 may make a determination using a method such as the method described in the first embodiment based on, for example, a first composite image acquired at the far point end Pf and a second composite image acquired at the quasi-far point end Pqf.

According to the second embodiment described above, in addition to providing a substantially similar effect to the first embodiment described earlier, by acquiring a total of, for example, four images while shifting a position of the focusing lens 11a in a configuration that enables a plurality of images (for example, two images) with different focus positions to be simultaneously acquired by the dividing optical system 16 and determining a transition to the proximity state based on magnitude relationship between contrast differences or a difference or a ratio between the contrast differences, high determination accuracy can be achieved without depending on a magnitude of a contrast of a subject itself.

Third Embodiment

Figure 11:
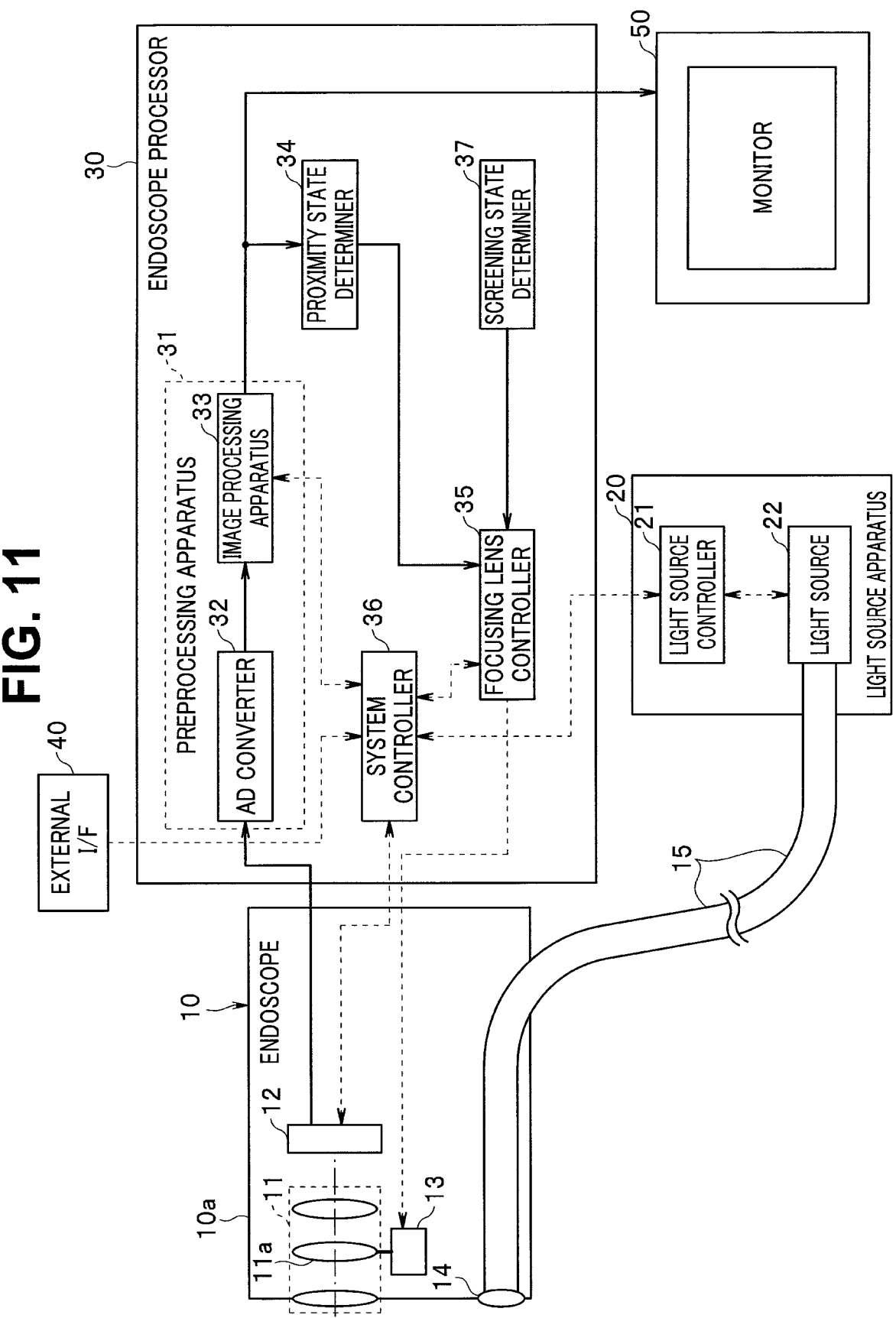
FIG. 11 is a block diagram showing structural and functional components of an endoscope system according to a third embodiment of the present invention.
Figure 12:
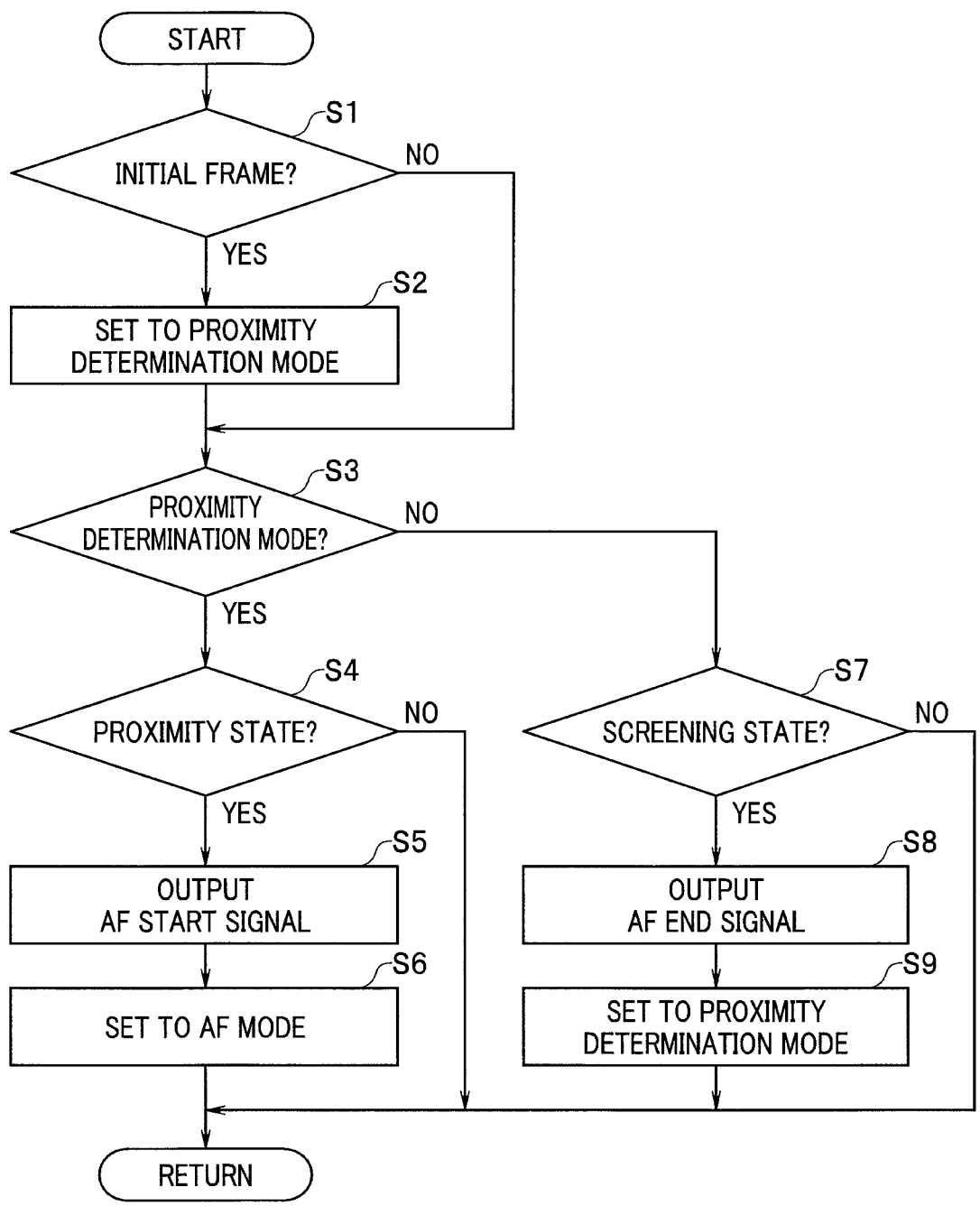
FIG. 12 is a flow chart showing an operation of the endoscope system according to the third embodiment of the present invention.

FIGS. 11 and 12 represent a third embodiment of the present invention, in which FIG. 11 is a block diagram showing structural and functional components of an endoscope system according to the third embodiment. In the third embodiment, portions similar to the first and second embodiments (including the modification of the first embodiment) described above will be denoted by same reference signs or the like and descriptions of such portions will be omitted as appropriate, and only differences will be mainly described.

In the endoscope system according to the present embodiment, the endoscope processor 30 further includes the screening state determiner 37.

The screening state determiner 37 determines whether or not a transition has been made from the proximity state to the screening state, and when the screening state determiner 37 determines that a transition has been made to the screening state, the screening state determiner 37 outputs an AF end signal to the focusing lens controller 35.

As described above, when the focusing lens controller 35 receives an AF end signal during control in the AF mode, the focusing lens controller 35 ends the AF mode and performs control in the proximity determination mode.

The determination by the screening state determiner 37 is performed according to, for example, a method described below.

For example, the screening state determiner 37 acquires, at appropriate time intervals from the moving mechanism 13 or the focusing lens controller 35, information on the position P of the focusing lens 11a being controlled in the AF mode. In addition, the screening state determiner 37 determines that a transition has been made to the screening state when the acquired position of the focusing lens 11a is, for example, the far point end Pf (however, the position of the focusing lens 11a is not limited to the far point end Pf and may be an appropriate position in a vicinity of the far point end Pf).

In addition, the endoscope 10 is configured to basically irradiate a subject with illuminating light from the light source apparatus 20 and to observe the subject by receiving reflected light from the subject in a state where ambient light (sunlight, indoor light, or the like) cannot be expected. Therefore, the subject becomes darker when the subject moves away from the distal end portion of the insertion portion 10a of the endoscope 10 and the subject becomes brighter when the subject approaches the distal end portion of the insertion portion 10a. Therefore, the screening state determiner 37 acquires a luminance value of an image from, for example, the image processing apparatus 33 in, for example, frame units. In addition, a determination that a transition has been made to the screening state may be made when, for example, an average of luminance values in an AF region in the acquired image becomes smaller than a predetermined threshold.

Furthermore, in the endoscope system, dimming for controlling a light amount of the light source 22 is performed so that the subject is illuminated at appropriate brightness. Therefore, for example, the screening state determiner 37 acquires the light amount of the light source 22 from the light source controller 21 via, for example, the system controller 36. In addition, the screening state determiner 37 may be configured to determine that a distance to the subject has increased or, in other words, a transition has been made to the screening state when the light amount of the light source 22 exceeds a predetermined threshold.

In addition, the screening state determiner 37 may adopt a determination method such as a method described below.

When the endoscope 10 is brought close to the subject, a motion vector of an image is oriented outwards in a direction of radiation (because when the distal end portion of the insertion portion 10a is brought close to the subject at center of the image, a subject portion having been near the center of the image moves to a peripheral side of the image).

Conversely, when the endoscope 10 is moved away from the subject, the motion vector of the image is oriented inwards in the direction of radiation (because when the distal end portion of the insertion portion 10a is moved away from the subject at the center of the image, a subject portion having been outside of an angle of view comes into the angle of view).

Therefore, the screening state determiner 37 acquires images of a plurality of frames that are temporally-continuous from the preprocessing apparatus 31, performs image recognition, and detects a motion vector. Furthermore, based on the detected motion vector, the screening state determiner 37 determines whether the distal end portion of the insertion portion 10a is approaching or moving away from a specific portion of the subject (whether the motion vector is outward or inward relative to the center of the image) and determines a movement speed (a magnitude of the motion vector). In addition, when a state of moving away continues for a predetermined time period or more, the screening state determiner 37 determines that a user is attempting to observe the subject from a farther distance or, in other words, a transition has been made to the screening state.

FIG. 12 is a flow chart showing an operation of the endoscope system according to the third embodiment. Note that FIG. 12 describes one frame's worth of processing contents and the processing shown in FIG. 12 is performed every time an image corresponding to one frame is acquired in main processing (not illustrated).

When entering the processing shown in FIG. 12 from the main processing (not illustrated), the system controller 36 determines whether or not a frame image is a first frame image (initial frame) to be acquired after starting the endoscope system (step S1).

At this point, when the present frame is determined to be the initial frame, the system controller 36 sets the focusing lens controller 35 to the proximity determination mode (step S2).

When processing of step S2 is performed or when the present frame is determined not to be the initial frame in step S1, the system controller 36 determines whether a present control mode is the proximity determination mode or the AF mode (step S3).

When the present control mode is determined to be the proximity determination mode (in other words, when a previous frame has been in the screening state), the proximity state determiner 34 determines whether or not a present frame is the proximity state (in other words, whether or not a transition has been made from the screening state of the previous frame to a proximity state in the present frame) (step S4).

When it is determined at this point that a transition has been made to the proximity state, the proximity state determiner 34 outputs an AF start signal to the focusing lens controller 35 (step S5).

When the focusing lens controller 35 receives the AF start signal, the focusing lens controller 35 sets the control mode to the AF mode, controls the focusing lens 11a via the moving mechanism 13, and performs autofocus so that a subject inside an AF region is continuously kept in focus (step S6).

In addition, when it is determined in step S3 that the present control mode is the AF mode (in other words, when the previous frame has been in the proximity state), the screening state determiner 37 determines whether or not the present state is the screening state (in other words, whether or not a transition has been made from the proximity state of the previous frame to the screening state in the present frame) (step S7).

At this point, when it is determined that a transition has been made to the screening state, the screening state determiner 37 outputs an AF end signal to the focusing lens controller 35 (step S8).

When the focusing lens controller 35 receives the AF end signal, the focusing lens controller 35 sets the control mode to the proximity determination mode, controls the focusing lens 11a via the moving mechanism 13, fixes a position of the focusing lens 11a basically to the far point end Pf as described earlier, and periodically or aperiodically performs a slight reciprocating operation of an amplitude A (step S9).

When it is determined in step S4 that the present state is not the proximity state, when the processing of step S6 is performed, when it is determined in step S7 that the present state is not the screening state, or when the processing of step S9 is performed, a return is made from the processing shown in FIG. 12 to the main processing (not illustrated).

Obviously, a configuration in which the screening state determiner 37 is provided separately from the proximity state determiner 34 as shown in FIG. 11 may be applied to the configuration of the second embodiment.

According to the third embodiment described above, in addition to providing a substantially similar effect to the first and second embodiments described earlier, since the screening state determiner 37 that is separate from the proximity state determiner 34 is provided to determine whether or not a transition has been made to the screening state, various determination methods can be applied and highly accurate determination can be achieved.

While a case where the present invention is an endoscope processor has been mainly described above, the present invention is not limited to the endoscope processor and may be a control method of a focusing lens that performs similar processing to the endoscope processor, a program that causes a computer to control an endoscope, a non-transitory storage medium that is readable by a computer storing the program, or the like.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope processor that can be connected to an endoscope including:
an objective optical system including a focusing lens and configured to form an optical image of a subject;
a moving mechanism configured to move the focusing lens; and
an image pickup apparatus configured to acquire an image by picking up the optical image,
the endoscope processor comprising a processor, wherein the processor is configured to:
control the moving mechanism in any one of an autofocus mode for automatically bringing the subject into focus and a proximity determination mode for determining whether or not a transition is made from a screening state to a proximity state;
execute the proximity determination mode when the autofocus mode is turned off;
during the proximity determination mode,
when a variation in an image height in an effective image range with control of the moving mechanism is 1% or less, determine whether or not a transition is made from the screening state to the proximity state based on positional information of the focusing lens and a change in the image; and when it is determined that a transition is made to the proximity state, end the proximity determination mode and control the moving mechanism in the autofocus mode.

2. The endoscope processor according to claim 1, wherein the processor is configured to further determine whether or not a transition is made from the proximity state to the screening state during control of the moving mechanism in the autofocus mode, and when it is determined that a transition is made to the screening state, end the autofocus mode and control the moving mechanism in the proximity determination mode.

3. The endoscope processor according to claim 1, wherein the processor is configured to move the focusing lens in at least a proximal direction when determining whether or not a transition is made from the screening state to the proximity state by moving the focusing lens so that a variation in an image height in the effective image range is 1% or less.

4. The endoscope processor according to claim 3, wherein a start point when the focusing lens is moved in the proximal direction is a far point end.

5. The endoscope processor according to claim 1, wherein the processor is configured to cause the focusing lens to perform a reciprocating operation so that a variation in an image height in the effective image range with the control of the moving mechanism is 1% or less.

6. The endoscope processor according to claim 1, wherein the processor is configured to determine whether or not a transition is made to the proximity state based on a difference or a ratio between a contrast value of an image acquired by the image pickup apparatus at a far point end and a contrast value of an image acquired by the image pickup apparatus at a position other than the far point end.

7. The endoscope processor according to claim 1, wherein the image pickup apparatus includes an image pickup device adopting an image plane phase-difference detection AF system, and the processor is configured to determine whether or not a transition is made to the proximity state based on a difference or a ratio between a phase difference acquired by the image pickup device at a far point end and a phase difference acquired by the image pickup device at a position other than the far point end.

8. The endoscope processor according to claim 1, wherein the endoscope further includes a dividing optical system configured to divide a luminous flux from the objective optical system into a plurality of luminous fluxes with different optical path lengths, and the image pickup apparatus is configured to pick up a plurality of optical images due to the plurality of luminous fluxes divided by the dividing optical system and simultaneously acquire a plurality of images with different focus positions.

9. The endoscope processor according to claim 1, wherein the processor is configured to set a region for determination for determining whether or not a transition is made to the proximity state with respect to an image acquired by the image pickup apparatus.

10. The endoscope processor according to claim 1, wherein
the processor is configured to:
calculate a reliability when the focusing lens is moved; and
determine, based on the change in the image, the positional information of the focusing lens, and the reliability, whether or not a transition is made from the screening state to the proximity state when the focusing lens is moved.

11. The endoscope processor according to claim 10, wherein
the processor is configured to calculate the reliability from at least one of a motion amount, luminance, a presence or absence of a reflection of a distal end of the endoscope, a presence or absence of a reflection of a treatment instrument, a light amount, an emission period, a charge readout period, or a wavelength of illuminating light.

12. A storage medium that is a non-transitory storage medium that is readable by a computer storing a program,
the program causing a computer controlling an endoscope to:
control a moving mechanism configured to move a focusing lens included in an objective optical system of the endoscope in any one of an autofocus mode for automatically bringing a subject into focus and a proximity determination mode for determining whether or not a transition is made from a screening state to a proximity state;
execute the proximity determination mode when the autofocus mode is turned off;
during the proximity determination mode,
when a variation in an image height in an effective image range is 1% or less, determine whether or not a transition is made from the screening state to the proximity state based on positional information of the focusing lens and a change in an image acquired by an image pickup apparatus included in the endoscope; and
when it is determined that a transition is made to the proximity state, end the proximity determination mode and control the moving mechanism in the autofocus mode.

* * * * *